United States Patent [19]

Fukushima et al.

[11] 4,129,565
[45] Dec. 12, 1978

[54] ISOCARBOSTYRIL DERIVATIVES

[75] Inventors: Hideo Fukushima, Saitama; Yoshikuni Suzuki, Kawagoe, both of Japan

[73] Assignee: Nisshin Flour Milling Co., Ltd., Tokyo, Japan

[21] Appl. No.: 751,522

[22] Filed: Dec. 16, 1976

Related U.S. Application Data

[63] Continuation-in-part of Ser. No. 703,502, Jul. 8, 1976, abandoned.

[30] Foreign Application Priority Data

Jul. 11, 1976 [JP] Japan ................... 51-83408
Jul. 9, 1976 [DE] Fed. Rep. of Germany ....... 2631080
Jul. 11, 1975 [GB] United Kingdom ............... 29335/75

[51] Int. Cl.$^2$ ................ C07D 217/16; C07D 217/24; C07D 401/12
[52] U.S. Cl. .................... 546/142; 424/250; 424/258; 544/363
[58] Field of Search ....... 260/288 D, 289 D, 268 BQ, 260/286 R, 286 Q, 288 CE

[56] References Cited

U.S. PATENT DOCUMENTS

| 3,910,924 | 10/1975 | Tamura et al. | 260/286 R |
| 4,013,663 | 3/1977 | Westermann et al. | 260/288 D |

FOREIGN PATENT DOCUMENTS

| 2447756 | 4/1975 | Fed. Rep. of Germany | 260/288 D |

Primary Examiner—Paul M. Coughlan, Jr.
Attorney, Agent, or Firm—Haseltine, Lake & Waters

[57] ABSTRACT

Isocarbostyrils of the formula

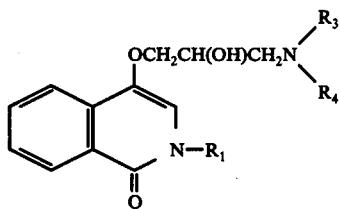

wherein $R_1$ represents a lower alkyl group having 1 to 4 carbon atoms, and $R_3$ and $R_4$, same or different, individually means hydrogen or an alkyl, aralkyl or cycloalkyl group provided at least either one of $R_3$ and $R_4$ should not be hydrogen, or $R_3$ and $R_4$ together with the adjacent nitrogen atom may form a heterocyclic ring, having anti-arrhythmic activity and low toxicity are prepared by reacting a 4-substituted isocarbostyril derivative of the formula

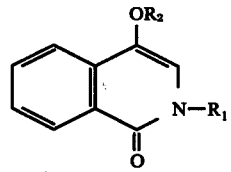
(I)

wherein $R_1$ is the same as defined above and $R_2$ represents

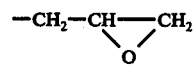

or its functional equivalent, e.g. —CH$_2$—CH(OH)CH$_2$X in which X represents a halogen atom, with an alkyl amine of the general formula

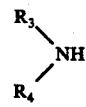

wherein $R_3$ and $R_4$ are same as defined above..

6 Claims, No Drawings

ISOCARBOSTYRIL DERIVATIVES

This application is a continuation-in-part application of Ser. No. 703,502 filed July 8, 1976, now abandoned.

This invention relates to 4-(3-mono- or di-substituted amino-2-hydroxy)propoxy-2-alkyl isocarbostyril derivatives and the non-toxic acid addition salt or quaternary salt thereof. More particularly, the invention pertains to 4-(3-substituted amino-2-hydroxy)propoxy-2-alkyl isocarbostyrils of the general formula

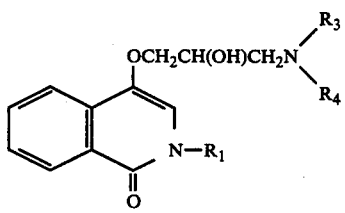  (I)

wherein $R_1$ represents a lower alkyl group having 1 to 4 carbon atoms, and $R_3$ and $R_4$, same or different, individually means hydrogen or an alkyl, aralkyl or cycloalkyl group provided that both $R_3$ and $R_4$ are not hydrogen, or $R_3$ and $R_4$ together with the adjacent nitrogen atom may form a heterocyclic ring.

The 4-(3-substituted amino-2-hydroxy)propoxy-2-alkyl isocarbostyril derivatives of the general formula (I) of the present invention have anti-arrhythic activity with the attendant low toxicity and are novel compounds useful for the treatment or prophylaxis of heart diseases.

In another aspect of the invention, there is provided a process for the preparation of 4-(3-substituted amino-2-hydroxy)propoxy-2-alkyl isocarbostyril derivatives, which comprises reacting a 4-substituted isocarbostyril derivative of the general formula

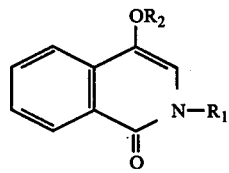  (II)

wherein $R_1$ is the same as defined above and $R_2$ represents

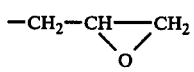

or its functional equivalent, e.g. —CH$_2$—CH(OH)CH$_2$X in which X represents a halogen atom, with an alkyl amine of the general formula

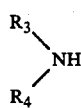  (III)

wherein $R_3$ and $R_4$ are same as defined above.

In the process according to the present invention, it is considered that when a 4-substituted isocarbostyril derivative of the general formula (II) in which $R_2$ represents —CH$_2$CH(OH)CH$_2$X (wherein X represents a halogen atom) is used in the reaction, the halogen containing compound reacts, either as it is or through the corresponding epoxide form of the general formula (II) in which $R_2$ represents

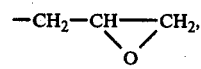

with an alkyl amine of the general formula (III).

As the 4-substituted isocarbostyril derivatives of the general formula (II) used in the reaction of the present invention, there may be exemplified, for example, 4-(2,3-epoxy)propoxy-2-methyl isocarbostyril, and likewise the alkylamines of the general formula (III) include, for example, isopropylamine, tert.-butylamine, sec.-butylamine benzylamine, cyclohexylamine, piperidine, piperazine, methylpiperazine, methylethylamine, diethylamine, and the like. The instant reaction may be carried out with or without organic solvents, preferably such lower alcohols as methanol, ethanol and the like.

The amount of the alkylamines of the general formula (III) used in the reaction is at least 1 mole per mole of, preferably 3 to 5 times the molar quantity of the 4-substituted isocarbostyril derivative of the general formula (II). The reaction can be carried out at any temperature from room temperature to elevated temperatures, and it usually is carried out at a temperature of from 50° to 100° C. The reaction time of about 3 to about 10 hours is sufficient for the above-specified temperature range.

To isolate a reaction product from the liquid reaction mixture resulted from the reaction, for example, the reaction mixture is distilled to remove the solvent therefrom and the residue is then purified by column chromatography on silica gel, thereby obtaining the reaction product in its form of a free base. The thus isolated free base may be converted, if desired, into a corresponding acid addition salt by treatment with such inorganic acids as hydrochloric and sulfuric or such organic acids as oxalic, succinic or maleic.

Of the compounds obtained according to the present invention, those which are of great importance include, for example, 4-(3-isopropylamino-2-hydroxy)propoxy-2-methyl isocarbostyril hydrochloride, 4-(3-tert.-butylamino-2-hydroxy)propoxy-2-methyl isocarbostyril hydrochloride and 4-(3-sec.-butylamino-2-hydroxy)propoxy-2-methyl isocarbostyril hydrochloride, as well as 4-(3-isopropylamino-2-hydroxy)propoxy-2-ethyl isocarbostyril hydrochloride, 4-(3-tert.-butylamino-2-hydroxy)propoxy-2-ethyl isocarbostyril hydrochloride and 4-(3-sec.-butylamino-2-hydroxy)propoxy-2-ethyl isocarbostyril hydrochloride.

The 4-(3-substituted amino-2-hydroxy)propoxy-2-alkyl isocarbostyril derivative of the general formula (I) wherein both of $R_3$ and $R_4$ are not hydrogen may, if desired, be reacted with an alkyl halide ($R_5X$) thereby to obtain the corresponding quaternary salt of the general formula

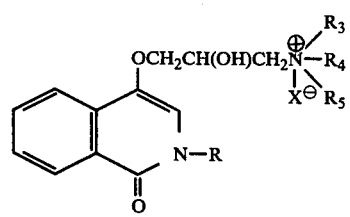

wherein $R_3$ and $R_4$ are same defined above provided that both of them are not hydrogen, $R_5$ is an alkyl group, and X is a halogen atom such as chlorine, bromine or iodine.

Typical representatives of the quaternary salts include: 4-(3-diethylamino-2-hydroxy)propoxy-2-methylisocarbostyril methoiodide ($R_3=R_4=C_2H_5$, $R_5=CH_3$, $X=I$); 4-(3-dimethylamino-2-hydroxy)-propoxy-2-methyl-isocarbostyril ethoiodide ($R_3=R_4=CH_3$, $R_5=C_2H_5$, $X=I$); 4-(3-dimethylamino-2-hydroxy)propoxy-2-methyl isocarbostyril isopropoxide ($R_3=R_4=CH_3$, $R_5=\text{iso-}C_3H_7$, $X=I$); 4-(3-diethylamino-2-hydroxy)propoxy-2-methyl isocarbostyril ethoiodide ($R_3=R_4=C_2H_5$, $R_5=C_2H_5$, $X=I$).

Furthermore, the 4-substituted isocarbostyril derivative of the general formula (II) used in the present invention is also a novel substance which is prepared, for example, by reaction of a 4-hydroxy-2-alkyl isocarbostyril with an epihalogenohydrin. This reaction is carried out in the presence of an inorganic or organic base such as alkali hydroxide, alkali carbonate, ammonium hydroxide, alkali metal alcoholate, pyridine or piperidine without or with organic solvents, for example, such lower alcohols as methanol and ethanol, such ethers as dioxane and the like, such ketones as acetone and the like, and such aromatic hydrocarbons as benzene and the like. Among these solvents, such lower alcohols as methanol, ethanol and the like are preferably used. Although it is not critical, the reaction usually is carried out at a temperature ranging from 40° to 70° C., and the reaction time of 1 to 7 hours is sufficient, for such temperature range.

The chemical substances of the general formula (I), which are the end products of the present invention, are concretely illustrated below with respect to their pharmacological activity.

In order to evaluate a β-adrenergic blocking effect of the isocarbostyril derivatives of the general formula (I) in comparison with propranolol as a control, experiments were conducted to determine antagonistic reaction against β-adrenergic stimulating effect due to isoproterenol in isolated guinea-pig atria and isolated guinea-pig tracheas.

Intrinsic heart stimulating effects of the compounds of the invention were also determined using reserpine-treated anaesthetized rats.

With respect to acute toxicity of the isocarbostyril derivatives of the general formula (I), experiments were carried out to obtain the $LD_{50}$ values of the compounds.

These experimental results obtained were summarized in Table I.

Table I

| Compounds | | | β-adrenergic blocking activity (Relative potency) | | Intrinsic heart stimulation | $LD_{50}$ mg/kg (mouse i.v.) |
|---|---|---|---|---|---|---|
| $R_1$ | $R_3$ | $R_4$ | atria ($\beta_1$) | trachea ($\beta_2$) | | |
| —CH$_3$ | H | —CH(CH$_3$)(CH$_3$) | 3.2 | 0.44 | 0 | 105 |
| —CH$_3$ | H | —C(CH$_3$)$_3$ | 2.5 | 0.52 | 0 | 119 |
| —CH$_3$ | H | —CH(CH$_3$)(C$_2$H$_5$) | 4.5 | 0.05 | 0 | 120 |
| Propranolol (Control) | | | 1 | 1 | 0 | 31 |

In clinical practice the compounds of the invention will normally be administered orally, rectally or by injection, in the form of pharmaceutical compositions containing the active ingredient either as a free base or as a pharmaceutically acceptable non-toxic acid addition salt, e.g. the hydrochloride, lactate, oxalate, succinate or malate, in association with a pharmaceutically acceptable carrier or diluent.

To produce pharmaceutical compositions containing a compound of the invention in the form of dosage units for oral administration, the selected compound may be mixed with a solid pulverulent carrier, e.g. lactose, saccharose, sorbitol, mannitol, a starch such as potato starch, corn starch, amylpectin, laminaria powder or citrus pulp powder, a cellulose derivative or gelatin, and a lubricant such as magnesium stearate, calcium stearate or polyethylene glycol wax, and then compressed to form tablets. If coated tablets are required, the cores, prepared as described above, may be coated with a concentrated sugar solution which may, for example, contain gum arabic, gelatin, talc or titanium dioxide. Alternatively, the tablet can be coated with a lacquer dissolved in a readily volatile organic solvent or mixture of organic solvents. Dyestuffs may be added to these coatings in order to readily distinguish between tablets containing different active compounds or different amounts of the active compound.

Pharmaceutical compositions suitable for oral administration suitably contain 2–50% by weight of active substance in admixture with 98–50% by weight of a solid pharmaceutically acceptable carrier or diluent.

Solutions for parenteral administration, e.g. by injection, can comprise aqueous solutions of a water-soluble pharmaceutically acceptable acid addition salt of the 4-(3-alkylamino-2-hydroxy)propoxy-2-alkyl isocarbostyril derivatives, preferably in a concentration of 0.5% to 10% by weight. Preferably the acid addition salt is the hydrochloride. These solutions may also contain stabilizing agents and/or buffering agents, and may conveniently be provided in various dosage unit ampoules.

Now the present invention will be further explained in reference to the following preparatory examples.

EXAMPLE 1

Preparation of 4-(3-isopropylamino-2-hydroxy)-propoxy-2-methylisocarbostyril hydrochloride In a stainless steel closed vessel were placed 10 g of 4-(2,3-epoxy)propoxy-2-methylisocarbostyril and 11.7 g of isopropylamine and heated at 100° C. for 7 hours. After completion of the reaction, the liquid reaction mixture was distilled to remove excess isopropylamine therefrom to obtain 14.6 g of a residual oily product.

The oily product thus obtained was dissolved in benzene, and the solution was absorbed on a silica gel column packed with 100 g of silica gel of 0.063–0.2 mm in size. The elution was effected first with benzene and then with 2% methanol-containing benzene and with 5% methanol-containing benzene. The eluates were combined and then distilled to remove the solvents therefrom, thereby isolating the end product in its form of a free base. To the thus isolated free base was added 50 ml of ether saturated with hydrogen chloride gas, and the mixture was allowed to stand overnight. The white, amorphous crystals deposited were washed with acetone and then vacuum dried to obtain 6.6 g of 4-(3-isopropylamino-2-hydroxy)propoxy-2-methyl isocarbostyril hydrochloride, m.p. 183°–185° C.

Elementary analysis: Calcd. for $C_{16}H_{22}N_2O_3 \cdot HCl$: C, 58.8%; H, 7.09%; N, 8.57%. Found: C, 58.7%; H, 7.00%; N, 8.60%.

IR (Nujol): 3300, 1640, 1620, 1590, 770 $cm^{-1}$. MNR (in $CD_3OD$) δ ppm:

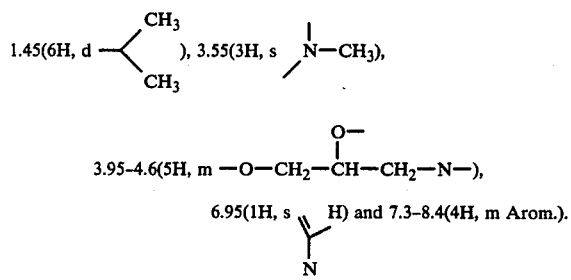

EXAMPLE 2

Preparation of 4-(3-tert.-butylamino-2-hydroxy)-propoxy-2-methylisocarbostyril hydrochloride To a solution of 10.5 g of 4-(2,3-epoxy)propoxy-2-methyl isocarbostyril in 100 ml of methanol was added 20 g of tert.-butylamine, and the mixture was refluxed for 6 hours. After completion of the reaction, the mixture is distilled to remove excess tert.-butylamine therefrom, thereby obtaining 14.2 g of a residual oily product.

The oily product thus obtained was dissolved in chloroform, and the solution was absorbed on a silica gel column packed with 100 g of silica gel of 0.063–0.2 mm in size. The elution was effected first with chloroform and then with 2% methanol-containing chloroform and with 5% methanol-containing chloroform. The eluates were combined and then distilled to remove the solvents therefrom, thereby isolating the end product in its form of a free base. To the thus isolated free base was added 50 ml of ether saturated with hydrogen chloride gas, and the mixture was allowed to stand overnight. The white, amorphous crystals deposited were filtered, washed with ethyl acetate and then vacuum dried to obtain 7.3 g of 4-(3-tert.-butylamino-2-hydroxy)-propoxy-2-methylisocarbostyril hydrochloride, m.p. 203°–205° C.

Elementary Analysis: Calcd. for $C_{17}H_{24}N_2O_3 \cdot HCl$: C, 59.9%; H, 7.39%; N, 8.22%. Found: C, 59.95%; H, 7.31%; N, 8.20%.

IR (Nujol): 3300, 1640, 1620, 1590, 770 $cm^{-1}$.
NMR (in $CD_3OD$) δ ppm:

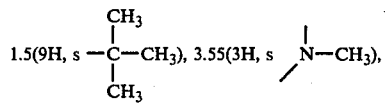

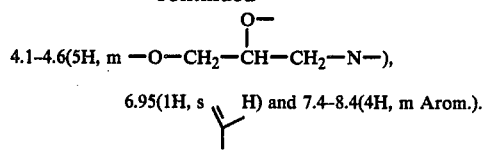

EXAMPLE 3

Preparation of 4-(3-sec.-butylamino-2-hydroxy)-propoxy-2-methyl isocarbostyril hydrochloride In a stainless steel closed vessel were placed 4 g of 4-(2,3-epoxy)propoxy-2-methylisocarbostyril and 7.56 g of sec.-butylamine, and the mixture was heated at 100° C. for 6 hours. After completion of the reaction, the liquid reaction mixture was treated and then purified in the same manner as in Example 1 to obtain 2.0 g of white, amorphous crystalline 4-(3-sec.-butylamino-2-hydroxy)propoxy-2-methylisocarbostyril hydrochloride, m.p. 110°–113° C.

Elementary Analysis: Calcd. for $C_{17}H_{24}N_2O_3 \cdot HCl$: C, 59.9%; H, 7.39%; N, 8.22%. Found: C, 59.83%; H, 7.4%; N, 8.14%. IR (Nujol): 3280, 1640, 1600, 780 $cm^{-1}$.

NMR (in $CD_3OD$) δ ppm:

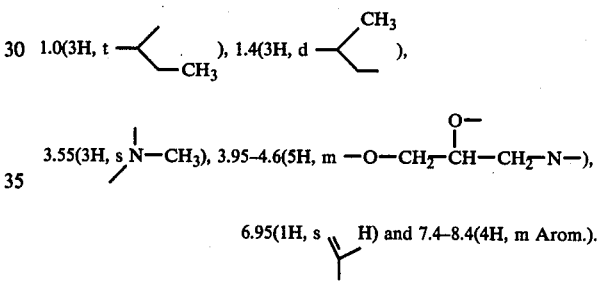

EXAMPLE 4

Synthesis of 4-(2,3-epoxy)propoxy-2-methylisocarbostyril

A mixture comprising 20 g of 4-hydroxy-2-methylisocarbostyril, 22 g of a 28% solution of sodium methylate in methanol and 52.6 g of epichlorohydrin was stirred at 50°–60° C. for 2 hours. The liquid reaction mixture was distilled to remove the methanol and epichlorohydrin therefrom, and the residue was dissolved in 100 ml of acetone. The acetone solution was filtered to remove undissolved matters and then distilled to remove the acetone therefrom, whereby crude crystals were deposited in the solution and collected by filtration. The thus obtained crude 4-(2,3-epoxy)propoxy-2-methyl isocarbostyril (20.2 g) was dissolved in 30 ml. of acetone and the resulting solution was chromatographed on a column packed with silica gel (0.063–0.2 mm in particle size, 100 g), with using acetone as an eluant. The eluant fractions were combined and concentrated, and then treated with 50 ml. of ethyl acetate. 7.0 g of white, amorphous crystalline 4-(2,3-epoxy)-propoxy-2-methyl isocarbostyril was obtained, 7.0 g, m.p. 130°–132° C.

Elementary Analysis: Calcd. for $C_{13}H_{13}NO_3$: C, 67.52%; H, 5.67%; N, 6.06%. Found: C, 67.48%; H, 5.69%; N, 6.10%. IR (Nujol): 1650, 1610, 1590, 1230, 760 $cm^{-1}$. NMR (in $CDCl_3$) δ ppm:

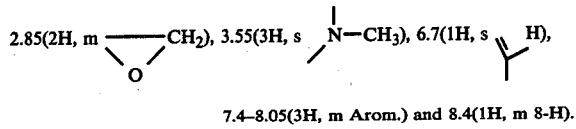

7.4–8.05(3H, m Arom.) and 8.4(1H, m 8-H).

EXAMPLE 5

Synthesis of 4-(2,3-epoxy)propoxy-2-methylisocarbostyril

A mixture comprising 4.4 g of 4-hydroxy-2-methylisocarbostyril, 7.2 g of sodium carbonate decahydrate, 10 g of epichlorohydrin and 50 ml of methanol was reluxed by heating for 6 hours. The liquid reaction mixture was treated in the same manner as in Example 4 to obtain 4.5 g of 4-(2,3-epoxy)propoxy-2-methylisocarbostyril.

EXAMPLE 6

Preparation of 4-(3-sec.-butylamino-2-hydroxy)propoxy-2-methyl isocarbostyril hydrochloride A mixture of 6.0 g of 4-hydroxy-2-methyl isocarbostyril, 41 g of epichlorohydrin and 0.1 ml of piperidine was heated at 90°–100° C. for 3 hours. The resulting reaction mixture was distilled to remove excess epichlorohydrin and the residue was washed with ethyl acetate. The thus obtained crude crystalline mass (6.5 g) was a mixture of 4-(2,3-epoxy)propoxy-2-methyl isocarbostyril and 4-(2-hydroxy-3-chloro)propoxy-2-methyl isocarbostyril (m.p. 133°–137° C.). 4.0 g of this mixture was brought into reaction with 7.56 g of sec.-butylamine in the same manner as mentioned in the preceding Example 3, thereby to obtain 2.0 g of 4-(3-sec.-butylamino-2-hydroxy)propoxy-2-methyl isocarbostyril hydrochloride.

EXAMPLE 7

Preparation of 4-(3-benzylamino-2-hydroxy)propoxy-2-methylisocarbostyril hydrochloride 3.0 g of 4-(2,3-epoxy)propoxy-2-methylisocarbostyril and 7.0 g of benzylamine were heated at 90°–100° C. for 3 hours. After completion of the reaction, the liquid reaction mixture was distilled to remove excess benzylamine therefrom. The residual mass was dissolved in 200 ml. of benzene. The resulting benzene solution was washed with water and dehydrated with a saturated sodium chloride solution. The benzene was removed by distillation. 6.25 g of the oily product was obtained.

The oily product thus obtained was dissolved in benzene, and the solution was absorbed on a silica gel column packed with 45 g of silica gel of 0.063–0.2 mm in size. The elution was effected first with 500 ml of benzene and then with 800 ml of 5% methanol-containing benzene and with 1,000 ml of 10% methanol-containing benzene. The eluates were combined and then distilled to remove the solvents therefrom, thereby isolating the title compound (2.75 g) in its form of a free base. To the thus isolated free base was added 50 ml of ether saturated with hydrogen chloride gas, and the mixture was allowed to stand overnight. The white, amorphous crystals deposited were washed with acetone and then vacuum dried to obtain 6.6 g of 4-(3-benzylamino-2-hydroxy)propoxy-2-methyl isocarbostyril hydrochloride, m.p. 159.5°–162.5° C.

IR (Nujol): 3200, 1650, 1620, 1600, 1570, 780 cm$^{-1}$.

EXAMPLE 8

Preparation of 4-(3-cyclohexylamino-2-hydroxy)propoxy-2-methylisocarbostyril hydrochloride 3.0 g of 4-(2,3-epoxy)propoxy-2-methylisocarbostyril and 6.45 g of cyclohexylamine were heated at 90°–100° C. for 1½ hours. The liquid reaction mixture was distilled to remove the excess amine and the residual mass was dissolved in 300 ml of ethyl acetate. The resulting ethyl acetate solution was worked up in the same manner as in Example 7. After purification, 2.45 g of the title compound was obtained as its free base in crystalline form. This free base was treated in the same manner as in Example 7 to obtain its hydrochloride. The title compound thus obtained was white amorphous crystalline. Yield 3.37 g, m.p. 103°–106° C.

IR (Nujol): 3250, 1640, 1620, 1590, 770 cm$^{-1}$.

EXAMPLE 9

Preparation of 4-(3-piperidino-2-hydroxy)propoxy-2-methylisocarbostyril hydrochloride 3.0 g of 4-(2,3-epoxy)propoxy-2-methylisocarbostyril and 5.52 g of piperidine were heated at 90°–100° C. for 1½ hours. The liquid reaction mixture was worked up in the same manner as in Example 7. After purification, 2.62 g of the title compound was obtained as its free base in oil form. This free base was treated in the same manner as in Example 7 to obtain its hydrochloride. The title compound thus obtained was white amorphous crystalline. Yield 2.3 g, m.p. 98°–101° C.

IR (Nujol): 3250, 1650, 1620, 1590, 770 cm$^{-1}$.

EXAMPLE 10

Preparation of 4-(3-diethylamino-2-hydroxy)propoxy-2-methyl isocarbostyril 6.0 g of 4-(2,3-epoxy)propoxy-2-methyl isocarbostyril and 9.5 g of diethylamine were heated under reflux for 7 hours. The liquid reaction mixture was worked up in the same manner as in Example 7. 3.25 g of 4-(3-diethylamino-2-hydroxy)propoxy-2-methyl isocarbostyril was obtained as pale yellow oil.

IR (oil): 3380, 1660, 1630, 1600, 780 cm$^{-1}$. MS: m/e = 304

EXAMPLE 11

Preparation of 4-(3-N-methyl-butylamino-2-hydroxy)propoxy-2-methyl isocarbostyril 3.0 g of 4-(2,3-epoxy)propoxy-2-methyl isocarbostyril and 5.65 g of N-methylbutylamine were heated under reflux for 2 hours. The liquid reaction mixture was worked up in the same manner as in Example 7. 2.8 g of the title compound was obtained as colorless oil.

IR (oil): 3380, 1660, 1630, 1600, 780 cm$^{-1}$. MS: m/e = 318

EXAMPLE 12

Preparation of 4-(3-N-methylpiperazino-2-hydroxy)propoxy-2-methyl isocarbostyril 3.0 g of 4-(2,3-epoxy)propoxy-2-methyl isocarbostyril and 6.5 g of N-methylpiperazine were heated at 90°–100° C. for 3 hours. The liquid reaction mixture was worked up in the same manner as in Example 7. 3.0 g of the title compound was obtained.

IR (oil): 3380, 1660, 1630, 1600, 780 cm$^{-1}$. MS: m/e = 331

The corresponding hydrochloride had the melting point of 213°–217° C. and its infrared analysis (nujol)

showed its absorption maximum at 3300, 1660, 1630, 1600 and 780 cm$^{-1}$.

EXAMPLE 13

Preparation of 4-(3-diethylamino-2-hydroxy)-propoxy-2-methyl isocarbostyril methoiodide 1.0 g of 4-(3-diethylamino-2-hydroxy)propoxy-2-methyl isocarbostyril was dissolved in 15 ml of benzene. The resulting solution was added with 1.2 g of methyl iodide and the mixture was stirred at room temperature for 3 days. The crystalline mass was collected by filtration and washed with 10 ml of benzene and then with 10 ml of ether. After vacuum drying, 1.3 g of the title compound was obtained as white amorphous crystals, m.p. 177°–180° C.

EXAMPLE 14

Preparation of 4-(3-dimethylamino-2-hydroxy)-propoxy-2-methyl carbostyril isopropoiodide 1.0 g of 4-(3-dimethylamino-2-hydroxy)propoxy-2-methyl isocarbostyril was dissolved in 16.5 ml of benzene. The resulting solution was added with 1.55 g of isopropyl iodide and the mixture was stirred at room temperature for 3 days. The crystalline mass was collected by filtration and washed with 10 ml of benzene. After vacuum drying, 1.0 g of the title compound was obtained as white amorphous crystals, m.p. 201°–204.5° C.

EXAMPLE 15

Preparation of 4-(3-dimethylamino-2-hydroxy)-propoxy-2-methyl isocarbostyril ethoiodide 1.68 g of 4-(3-dimethylamino-2-hydroxy)propoxy-2-methyl isocarbostyril was dissolved in 20 ml of acetone. The resulting solution was added with 2.42 g of ethyl iodide and the mixture was stirred at room temperature overnight. The crystalline mass was collected by filtration and washed with 20 ml of acetone. After vacuum drying, 1.2 g of the title compound was obtained as white amorphous crystals, m.p. 162°–166° C.

EXAMPLE 16

Preparation of 4-(3-diethylamino-2-hydroxy)-propoxy-2-methyl isocarbostyril ethoiodide 1.5 g of 4-(3-diethylamino-2-hydroxy)propoxy-2-methyl isocarbostyril was dissolved in 20 ml of acetone. The resulting solution was added with 1.96 g of ethyl iodide and the mixture was stirred at room temperature overnight. The crystalline mass was collected by filtration and washed with 20 ml of acetone. After vacuum drying, 1.0 g of the title compound was obtained as white amorphous crystals, m.p. 209°–212° C.

The anti-arrhythic activity of the compounds in the present invention was determined according to Sekiya & Vanghan Williams' method disclosed in British Journal of Pharmacology 21, 462 (1963), and the results are shown below. In the table, +++, ++ or + indicate that the compound concerned is effective at the dose of 1 mg/kg, 3 mg/kg or 10 mg/kg, respectively, while — indicates no effect.

| $R_3$ | $R_4$ | $R_5$ | X | Anti-arrhythic activity | $LD_{50}$ (mg/kg, mouse, i.v.) |
|---|---|---|---|---|---|
| H | $-CH(CH_3)_2$ | — | — | +++ | 105 |
| H | $-C(CH_3)_3$ | — | — | ++ | 119 |
| H | $-CH(CH_3)(C_2H_5)$ | — | — | +++ | 120 |
| H | -n-$C_3H_7$ | — | — | ++ | 115 |
| H | -n-$C_4H_9$ | — | — | +++ | 105 |
| H | -n-$C_6H_{13}$ | — | — | ++ | 69 |
| H | $-CH_2-C_6H_5$ | — | — | + | 120 |

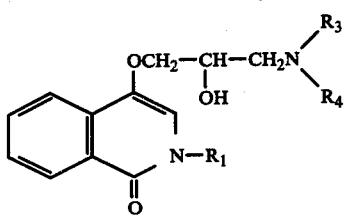

| R₃ | R₄ | R₅ | X | Anti-arrhythic activity | LD₅₀ (mg/kg, mouse, i.v.) |
|---|---|---|---|---|---|
| H | cyclohexyl | — | — | + | 80 |
| —CH₃ | -n-C₄H₉ | — | — | + | 143 |
|  | piperidino | — | — | + | 200 |
|  | 4-methylpiperazino | — | — | + | 270 |
| —C₂H₅ | —C₂H₅ | —CH₃ | I | + | 15.2 |
| —CH₃ | —CH₃ | —C₂H₅ | I | + | 16.7 |
| —CH₃ | —CH₃ | —CH(CH₃)₂ | I | + | <20 |

What we claim is:

1. A 4-(3-substituted amino-2-hydroxy) propoxy-2-alkyl isocarbostyril compound of the formula wherein $R_1$ represents $C_1$ to $C_4$ alkyl, and $R_3$ and $R_4$ individually means hydrogen, $C_1$ to $C_6$ alkyl, benzyl or cyclohexyl provided that both $R_3$ and $R_4$ are not hydrogen, or alternatively $R_3$ and $R_4$, together with their adjacent nitrogen atom, is piperidino, piperazino or methylpiperazino, the acid addition salt or quaternary salt thereof.

2. A 4-(3-substituted amino-2-hydroxy)propoxy-2-alkylisocarbostyril compound as claimed in claim 1, wherein said compound is in the form of an acid addition salt with an inorganic or organic acid.

3. A 4-(3-substituted amino-2-hydroxy)propoxy-2-alkylisocarbostyril compound as claimed in claim 1, said compound is in the form of a quaternary salt with an alkyl iodide.

4. 4-(3-isopropylamino-2-hydroxy)propoxy-2-methylisocarbostyril hydrochloride.

5. 4-(3-tert.-butylamino-2-hydroxy)propoxy-2-methylisocarbostyril hydrochloride.

6. 4-(3-sec.-butylamino-2-hydroxy)propoxy-2-methyl isocarbostyril hydrochloride.